US00PP36411P3

(12) United States Plant Patent
Boches et al.

(10) Patent No.: US PP36,411 P3
(45) Date of Patent: Jan. 28, 2025

(54) BLUEBERRY PLANT NAMED 'FCM14-057'

(50) Latin Name: *Vaccinium corymbosum*
Varietal Denomination: FCM14-057

(71) Applicant: Fall Creek Farm and Nursery, Inc., Lowell, OR (US)

(72) Inventors: Peter Stefan Boches, Hilo, HI (US); Antonio Alamo Bermudo, Seville (ES)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 0 days.

(21) Appl. No.: 18/421,292

(22) Filed: Jan. 24, 2024

(65) Prior Publication Data

US 2024/0251688 P1 Jul. 25, 2024

Related U.S. Application Data

(60) Provisional application No. 63/440,976, filed on Jan. 25, 2023.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

(56) References Cited

U.S. PATENT DOCUMENTS

PP27,623 P3 1/2017 Brazelton et al.
PP29,468 P3 7/2018 Brazelton et al.

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

The new blueberry plant 'FCM14-057' is provided. 'FCM14-057' is a commercial variety intended for the hand harvest fresh market. The variety is produced from a cross of 'FL01-06' (female parent, unpatented) and 'FF04-14' (male parent, U.S. Plant Pat. No. 27,623 plant), which can be distinguished by its outstanding features. 'FCM14-057' displays an upright medium vigor bush. The production time of this new variety is early to mid-season.

7 Drawing Sheets

Latin name of the genus and species:
Genus—*Vaccinium.*
Species—*corymbosum.*
Variety denomination: The new blueberry plant claimed is of the variety denominated 'FCM14-057'.

STATEMENT REGARDING FEDERALLY-SPONSORED RESEARCH AND DEVELOPMENT

None.

STATEMENT REGARDING PRIOR DISCLOSURES BY THE INVENTOR

The first sale of the new variety was Sep. 12, 2023, in the United States. The first sale of the new variety was by the inventor(s) or another who obtained the new variety directly or indirectly from the inventor(s). No plants of the new variety have been sold or offered for sale in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new blueberry plant of the present invention was created by controlled breeding from a cross of 'FL01-06'

(female parent, unpatented) and 'FF04-14' (male parent, U.S. Plant Pat. No. 27,623) in 2012 in Lowell, Oregon. The seeds resulting from the above cross were sown and small plants were obtained which were physically and biologically different from each other. Selective study in 2014 in Tala, Mexico resulted in the identification of a single plant of the new variety. 'FCM14-057' was selected in 2014. 'FCM14-057' was initially asexually reproduced by softwood cutting in 2014 from the original seedling in Tala, Mexico.

The new plant 'FCM14-057' has been planted in replicated trials from 2015-2016 in Tala, Jalisco Mexico.

'FCM14-057' has been found to undergo asexual propagation by soft wood cuttings in Tala, Jalisco, Mexico. Asexual propagation techniques in Tala, Jalisco, Mexico, such as soft wood cuttings, have shown that the characteristics of the new variety are homogenous, stable, and strictly transmissible by such asexual propagation from one generation to another. Accordingly, the new variety undergoes asexual propagation in a true-to-type manner with all the characteristics, as herein described, firmly fixed and retained through successive generations of such asexual reproduction.

SUMMARY OF THE INVENTION

The following traits have been repeatedly observed in Tala, Jalisco Mexico and it was found that the new blueberry plant 'FCM14-057' possesses the following combination of characteristics:

1. Early to mid-season production time,
2. Mild aromatic berry flavor,
3. Medium plant vigor, and
4. Upright growth habit.

The new variety of the present invention can readily be distinguished from its ancestors. More specifically, 'FL01-06' (i.e., the female parent) while grown in Tala, Mexico produces a low vigor bush compared to the medium vigor plant of the new variety 'FCM14-057'. Also, the fruit of 'FCM14-057' is darker than the fruit produced by the female parent. In addition, 'FF04-14' (i.e., the male parent) is a vigorous, round shaped plant versus the new variety 'FCM14-057' which has medium vigor and upright plant shape. Also, the fruiting season of 'FCM14-057' is earlier than 'FF04-14', and 'FCM14-057' produces a lighter blue colored fruit than 'FF04-14'. Moreover, the new variety can be readily distinguished from other similar non-parental varieties. For example, 'Biloxi' (unpatented) produces fruit which are smaller and lighter in color compared to fruit produced by the new variety.

BRIEF DESCRIPTION OF THE DRAWINGS

The accompanying photographic illustrations show typical specimens in full color of the foliage and fruit of the new variety 'FCM14-057', which were five years of age. The colors are as nearly true as is reasonably possible in a color representation of this type. The colors in the photographs are as close as possible with the photographic and printing technology utilized. The color values cited in the detailed botanical description accurately describe the colors of the new blueberry.

DETAILED BOTANICAL DESCRIPTION

Figure 1:
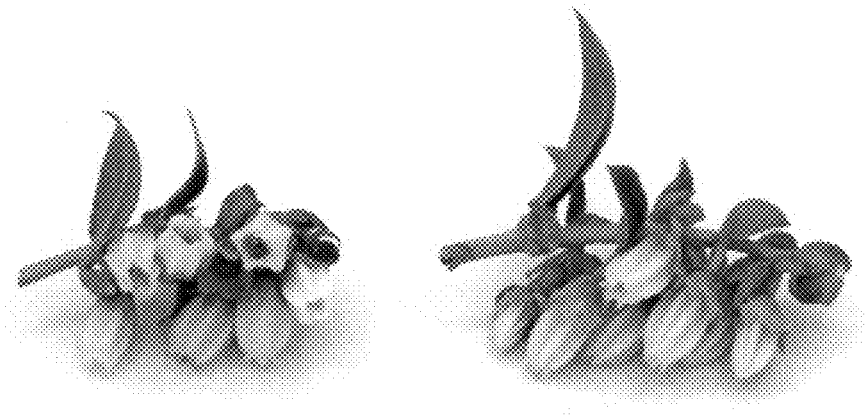
FIG. 1—depicts flower clusters of the new variety on typical primocanes.
Figure 2:
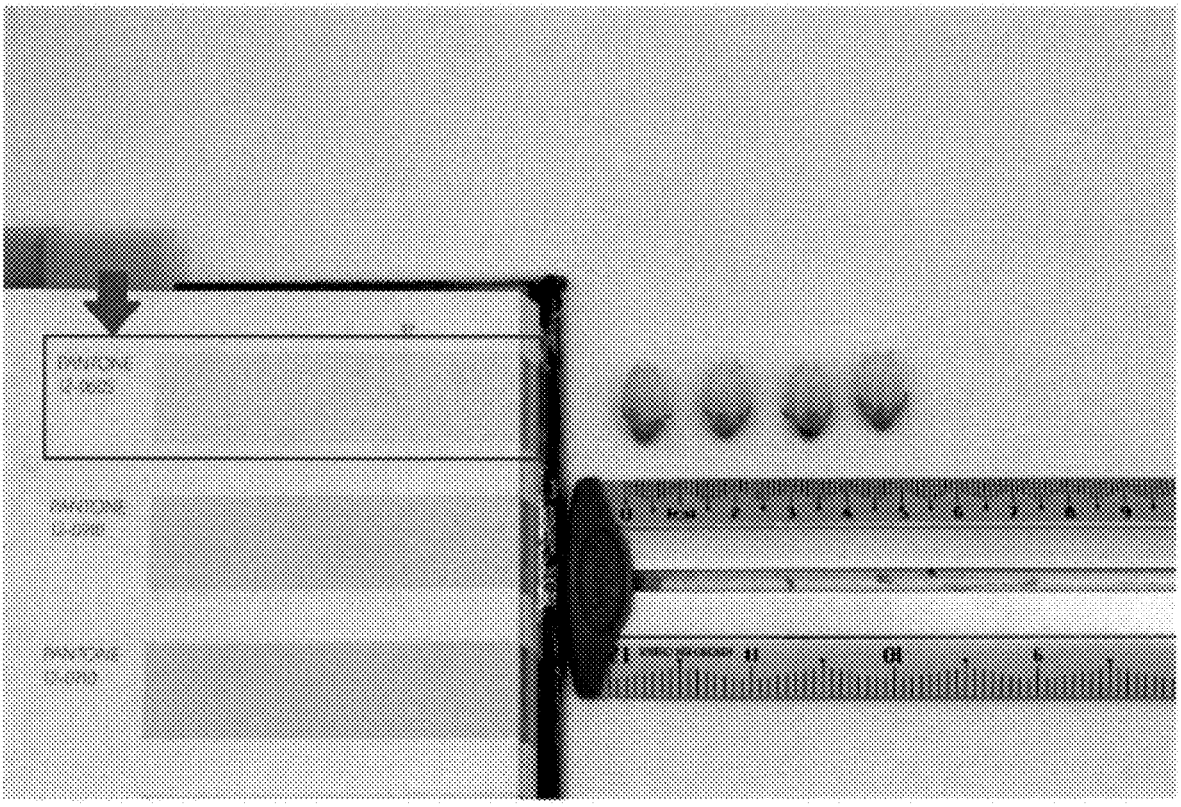
FIG. 2—depicts flowers of the new variety next to the pantone color chart and scale measured in millimeters.
Figure 3:
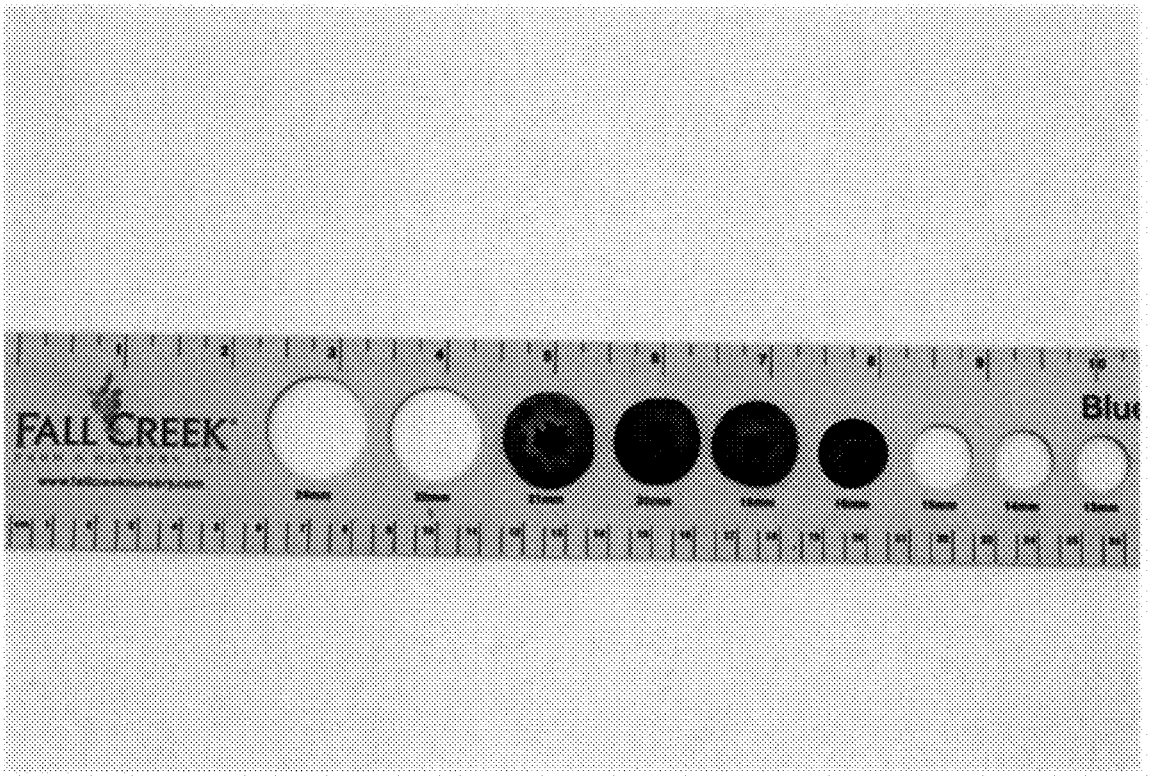
FIG. 3—depicts fruit of the new variety showing the average diameter fruit size measured in millimeters.
Figure 4:
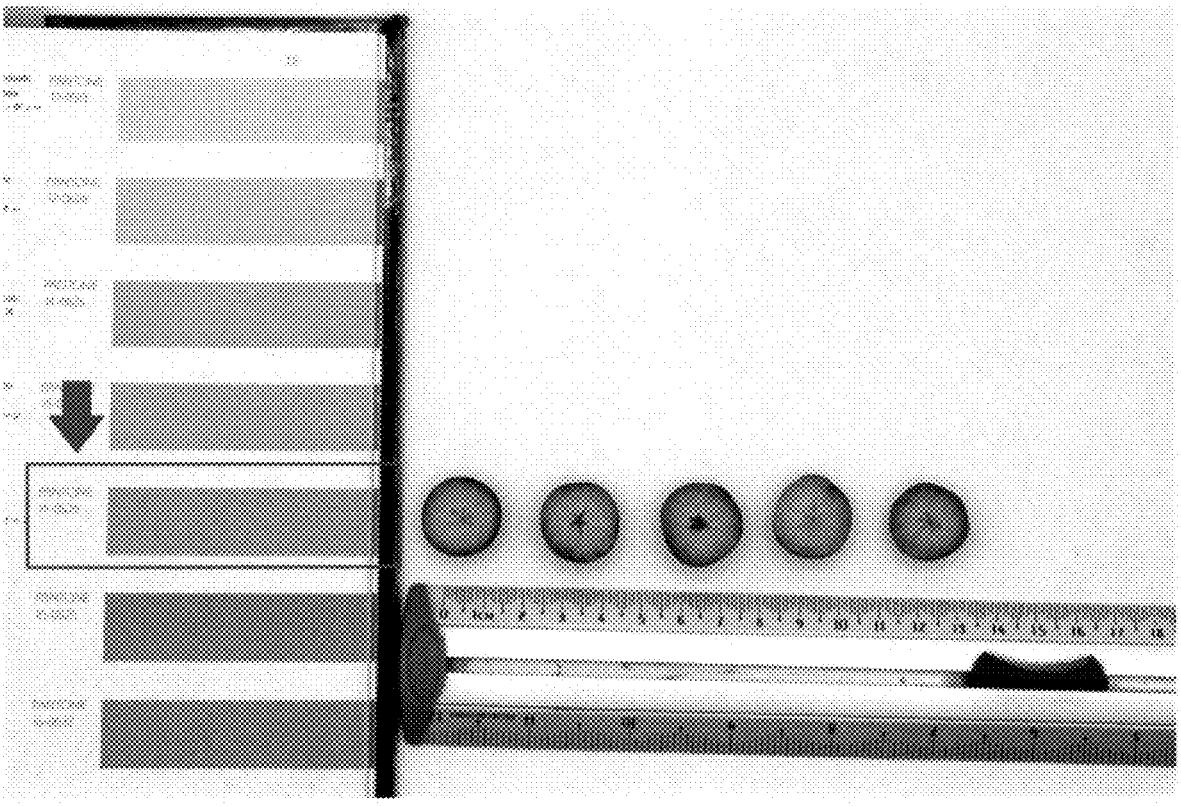
FIG. 4—depicts the flesh color on ripe fruit of the new variety, next to the pantone color chart and scale measured in millimeters.
Figure 5:
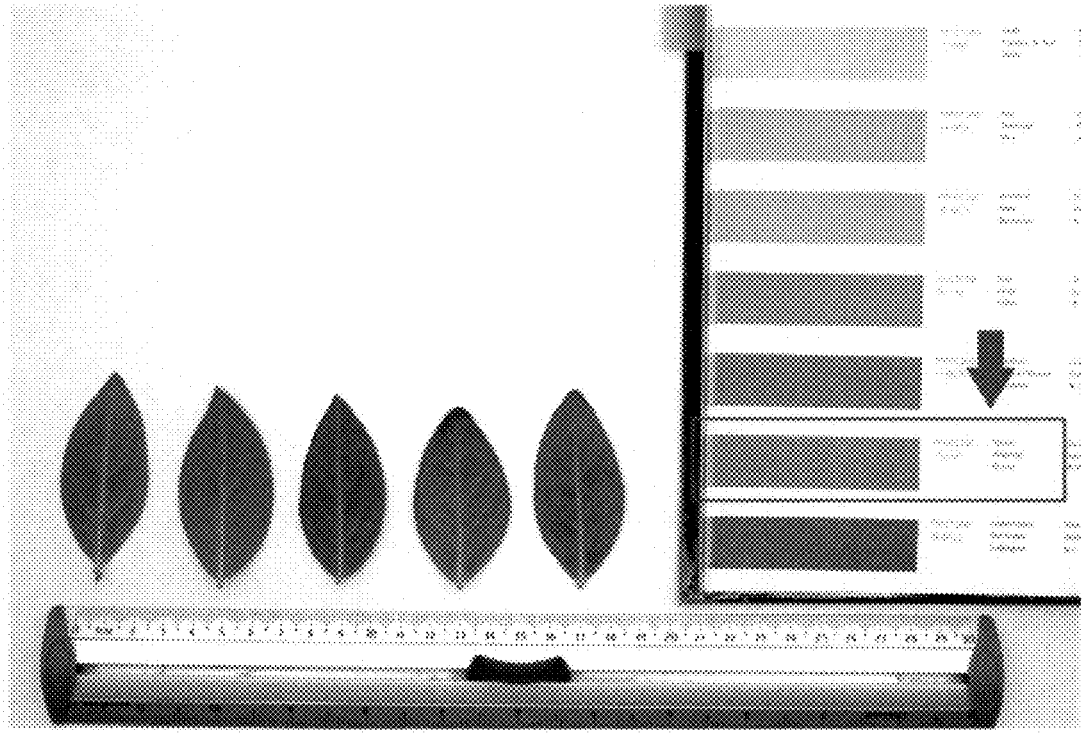
FIG. 5—depicts the average underside leaf color of the new variety next to the pantone color chart and scale measured in millimeters.
Figure 6:
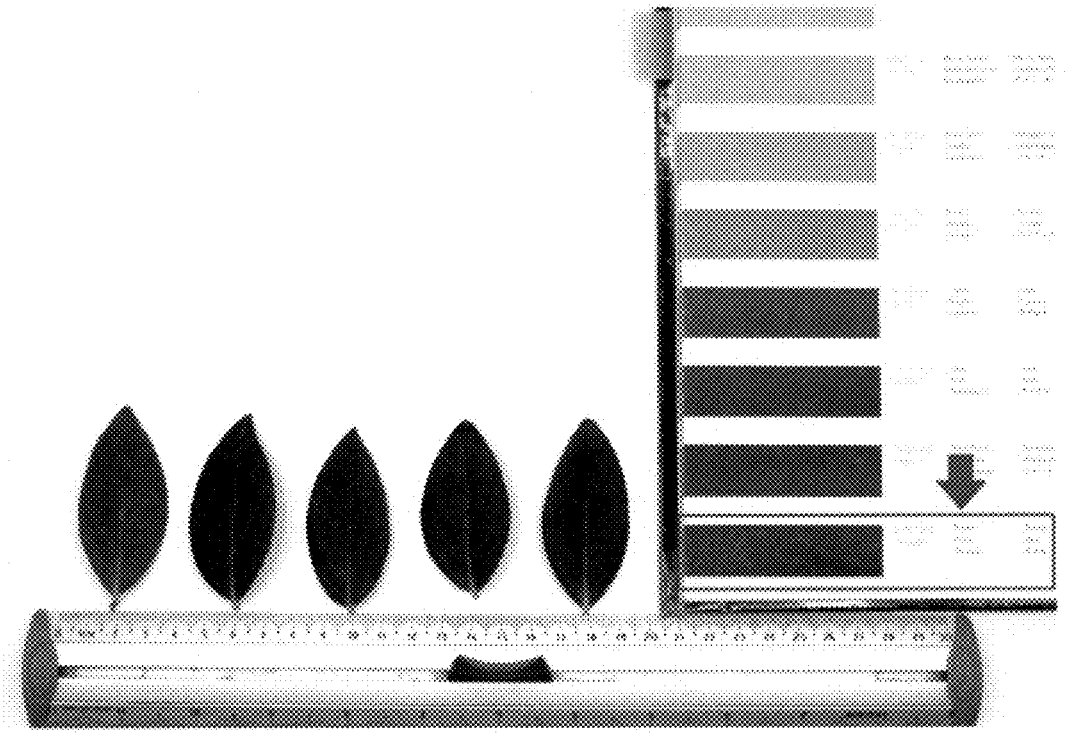
FIG. 6—depicts the average upper side leaf color of the new variety next to the pantone color chart and scale measured in millimeters.
Figure 7:
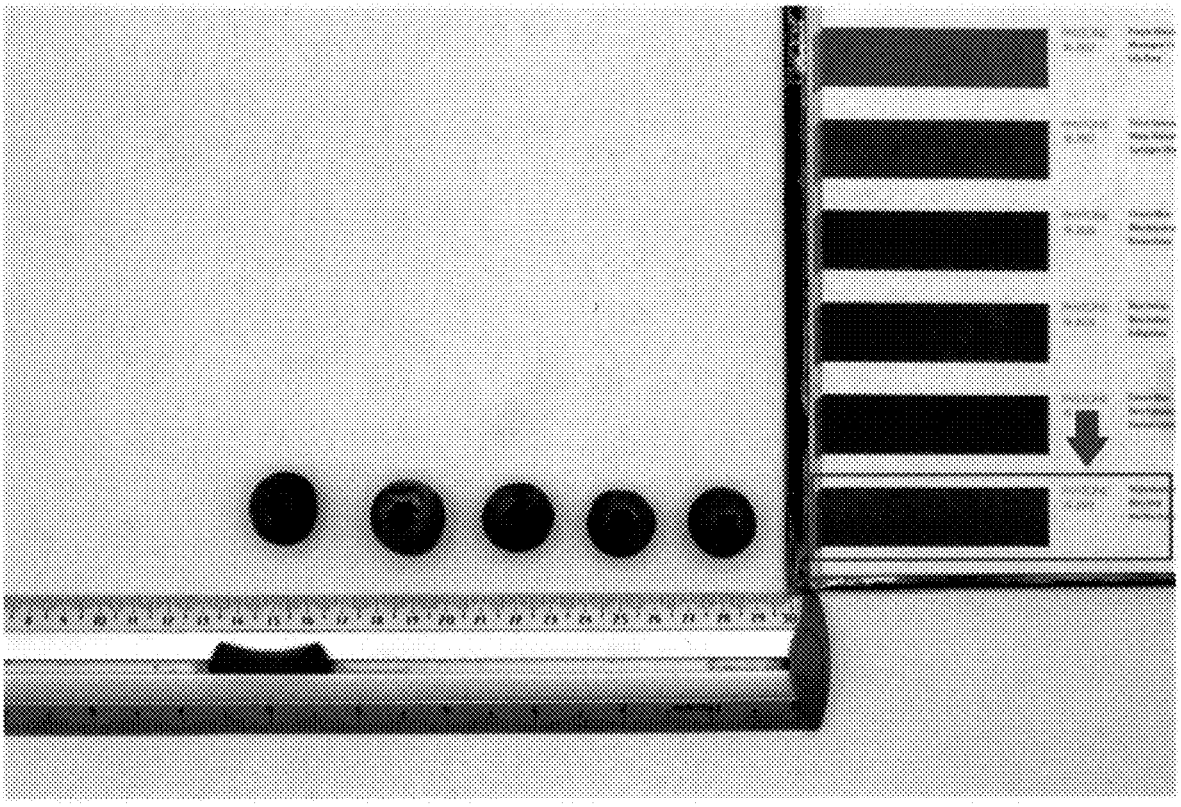
FIG. 7—depicts the average color of fruit of the new variety after removal from bloom next to the pantone color chart and scale measured in millimeters.

The following detailed description sets forth the distinctive characteristics of 'FCM14-057'. The data which defines these characteristics was collected from asexual reproductions of the original selection. Dimensions, sizes, colors, and other characteristics are approximations and averages set forth as accurately as possible. The plant history was taken on plants approximately 4 to 5 years of age, and the descriptions relate to plants grown in the field in Tala, state of Jalisco, Mexico. Descriptions of fruit characteristics were made on fruit grown in Tala, state of Jalisco, Mexico. Color designations are from "The Pantone Book of Color" (by Leatrice Eiseman and Lawrence Herbery, Harry N. Abrams, Inc., Publishers, New York 1990) unless noted otherwise and the color designations used herein represent the closest color observed on the majority of the specified botanical feature. Where the Pantone color designations differ from the colors in the photographs, the Pantone colors are accurate.

The new blueberry plant 'FCM14-057' has not been observed under all possible environmental conditions. The phenotype may vary somewhat with variations in environment and cultural practices, such as temperature and light intensity, without any variance in genotype.

GENERAL

Classification:
*Family*.—Ericaceae.
*Genus*.—*Vaccinium*.
*Species*.—*Corymbosum*.
*Common name*.—Southern Highbush Blueberry.

Parentage:
*Female parent*.—'FL01-06' (unpatented).
*Male parent*.—'FF04-14' (U.S. Plant Pat. No. 27,623).

Market class: Commercial blueberry variety intended for the hand harvest fresh market.

PLANT

General:
*Plant height*.—145.2 cm.
*Plant width*.—108 cm.
*Growth habit*.—Upright.
*Growth*.—Medium vigor, with several canes coming from the crown.
*Productivity*.—High.
*Cold hardiness*.—Not determined.
*Cold tolerance*.—Not determined.
*Chilling requirement*.—Estimated 0-500 chill hours, Utah Model.
*Resistance/susceptibility to root rot* (*phytopthora cinnamomii*).—Not overly susceptible.
*Resistance/susceptibility to stem blight* (*botryosphaeria sp.*).—Not overly susceptible.
*Resistance/susceptibility to phomopsis twig blisht* (*phomopsis vaccinii*).—Not overly susceptible.
*Resistance/susceptibility to botrytis* (*botrytis cinerea*).—Not overly susceptible.
*Resistance/susceptibility to leaf spot* (*septoria spp.*).—Not overly susceptible.
*Resistance/susceptibility to leaf rust* (*naohidemyces vaccinii*).—Not overly susceptible.
*Resistance/susceptibility to bud mites* (*acalatus vaccinii*).—Not overly susceptible.
*Leafing*.—Good leafing.
*Twigginess*.—Medium.

STEM

General:
*Suckering tendency*.—Medium.
*Mature cane color*.—Camel 17-1224.
*Mature cane length*.—65 cm.
*Mature cane width*.—3.12 cm.
*Bark texture*.—Rough.
*Fruit wood color*.—Green Oasis 15-0538.
*Fruit wood length*.—13.96 cm.
*Fruit wood diameter*.—3.04 mm.
*Fruit wood texture*.—Smooth.
*Fall color on new shoots*.—Apple Green 15-0543.

*Surface texture of new wood*.—Smooth.
*Internode length on strong, new shoots*.—15.44 mm.
*Average number of buds per fruiting lateral*.—7 buds.

FOLIAGE

General:
*Time of beginning of leaf bud burst*.—Late March.
*Leaf color* (*top side*).—Chive 19-0323.
*Leaf color* (*under side*).—Bluish Olive 18-0316.
*Fall leaf color* (*top side*).—Chive 19-0323.
*Fall leaf color* (*under side*).—Bluish Olive 18-0316.
*Leaf arrangement*.—Alternate.
*Leaf shape*.—Ovate.
*Leaf margins*.—Entire.
*Undulation of margin*.—Entire.
*Leaf venation*.—Anastomosing.
*Leaf apices*.—Acuminate.
*Leaf bases*.—Obtuse.
*Leaf length*.—72.32 mm.
*Leaf width*.—39.2 mm.
*Leaf length/width ratio*.—1.87 ratio.
*Leaf nectarines*.—Absent.
*Pubescence of upper side*.—Absent.
*Pubescence of lower side*.—Absent.
*Cross sectional profile*.—Undulate.
*Longitudinal profile*.—Entire.
*Attitude*.—Recurved.
Petioles:
*Length*.—4.7 mm.
*Width*.—2.74 mm.
*Color*.—Dried Moss 14-0626.
*Texture*.—Smooth.

FLOWERS

General:
*Time of beginning of flowering*.—Mid July.
*Time of* 50% *anthesis*.—Early September.
*Flower shape*.—Urceolate.
*Flower bud density*.—Medium.
*Flower fragrance*.—Mild floral sweet.
Corolla:
*Color*.—Bone White 12-0105.
*Length*.—10.4 mm.
*Width*.—7.89 mm.
*Aperture width*.—3.3 mm.
*Anthocyanin coloration of corolla*.—Absent.
*Corolla ridges*.—Distinct.
*Protrusion of stigma*.—Does not protrude.
Inflorescence:
*Length*.—52.1 mm.
*Diameter*.—33.3 mm.
*Length of peduncle*.—37.7 mm.
*Surface texture of peduncle*.—Rough.
*Color of peduncle*.—Green Oasis 15-0538.
*Length of pedicel*.—11.6 mm.
*Surface texture of pedicel*.—Rough.
*Color of pedicel*.—Apple Green 15-0543.
*Number of flowers per cluster*.—7.5 average.
*Flower cluster density*.—Medium.
Calyx (with sepals):
*Diameter*.—6.7 mm.
*Color* (*sepals*).—Lettuce Green 13-0324.
*Texture*.—Smooth.
Stamen:
*Length*.—5.7 mm.
*Number per flower*.—10.
*Filament color*.—Inca Gold 17-1048.
Pistil:
*Length*.—9.31 mm.
*Ovary color* (*exterior*).—Green Banana 14-0434.
*Style*.—Length — 4.6 mm.
*Color*.—Inca gold 17-1048.
Anther:
*Length*.—2.4 mm.
*Number per flower*.—10.
*Color*.—Buckskin 16-1342.
Pollen:
*Abundance*.—High.
*Color*.—Mellow Yellow 12-0720.
*Self-compatibility*.—High.

FRUIT

General:
*Time of fruit ripening*.—Early September.
*Time of* 50% *maturity*.—Mid November.
*Fruit development period*.—Average 66 days from bloom to blue.
*Fruit generally produced*.—The fruit mainly come from primocane buds, however, it will produce from resting buds later in the season.
*Mean harvest date*.—November $5^{th}$.
*Mean date of last pick*.—March $1^{st}$.
*Cluster density*.—Medium.
*Berries per cluster*.—Average 7.
*Unripe berry color*.—Lettuce Green 13-0324.
*Ripe berry color*.—Dappley Gray 16-3907.
*Berry skin color after polishing*.—Dark Navy 19-4013.
*Berry surface wax abundance*.—Medium.
*Berry flesh color*.—Water Lily 11-0304.
*Berry weight*.—3.34 gram per berry.
*Berry height from calyx to scar*.—17.4 mm.
*Berry diameter*.—23.2 mm.
*Calyx aperture*.—5.3 mm.
*Calyx depth*.—3.4 mm.
*Pedicel length*.—11.6 mm.
*Pedicel diameter*.—3.1 mm.
*Pedicel surface texture*.—Smooth.
*Pedicel color*.—Apple Green 15-0543.
*Berry detachment force*.—Medium difficult.
*Berry shape*.—Elliptic.
*Berry stem scar*.—Medium.
*General flavor*.—Mildly aromatic and balanced between sweetness and acidity, with a crispy, melting, juicy texture.
*Sweetness when ripe*.—Medium.
*Firmness when ripe*.—High.
*Acidity when ripe*.—Medium.
*Storage quality*.—Great storage at 28 days at 6 degrees Celsius.
*Suitability for mechanical harvesting*.—Low.
*Self-fruitfulness*.—85% fruit set.
*Uses*.—Fresh.

SEED

General:
*Seed abundance in fruit*.—11.4 seeds per berry average.
*Seed color*.—Almond 16-1432.
*Seed dry weight*.—7.9 mg per 100 seeds average.
*Seed length*.—2.02 mm.

COMPARISON BETWEEN PARENTAL AND COMMERCIAL CULTIVARS

TABLE 1

Comparison Table

| Denomination of similar variety | Characteristic for comparison | State of expression of similar variety | State of expression of candidate variety ('FCM14-057') |
|---|---|---|---|
| 'Biloxi' (unpatented) | Berry: Size | Small to medium | Medium to Jumbo |
| 'Biloxi' (unpatented) | Berry: Color | Light blue | Medium Dark |
| 'Biloxi' (unpatented) | Plant: Vigor | High | Medium |

TABLE 1-continued

Comparison Table

| Denomination of similar variety | Characteristic for comparison | State of expression of similar variety | State of expression of candidate variety ('FCM14-057') |
|---|---|---|---|
| 'FCM12-045' (U.S. Plant Patent No. PP29468) | Fruit: Firmness | Medium | Firm |
| 'FCM12-045' (U.S. Plant Patent No. PP29468) | Fruit: Storage Quality at 28 Days. | Medium | High |

The invention claimed is:

1. A new and distinct variety of blueberry plant named 'FCM14-057' substantially as illustrated and described herein.

* * * * *